(12) United States Patent
Wang

(10) Patent No.: US 11,826,510 B1
(45) Date of Patent: Nov. 28, 2023

(54) HFNC SYSTEM

(71) Applicant: Telesair, Inc., Irvine, CA (US)

(72) Inventor: Qing Wang, Palo Alto, CA (US)

(73) Assignee: Telesair, Inc., Irvine, CA (US)

( * ) Notice: Subject to any disclaimer, the term of this patent is extended or adjusted under 35 U.S.C. 154(b) by 0 days.

(21) Appl. No.: 18/315,645

(22) Filed: May 11, 2023

(51) Int. Cl.
*A61M 16/06* (2006.01)
*A61M 16/00* (2006.01)

(52) U.S. Cl.
CPC .... *A61M 16/0672* (2014.02); *A61M 16/0003* (2014.02); *A61M 2202/0208* (2013.01)

(58) Field of Classification Search
CPC .......... A61M 16/0066; A61M 16/0666; A61M 16/0672
See application file for complete search history.

(56) References Cited

U.S. PATENT DOCUMENTS

| | | | |
|---|---|---|---|
| 7,448,382 B1 * | 11/2008 | Alexander | A61M 16/0063 128/204.23 |
| 2007/0277827 A1 * | 12/2007 | Bordewick | A61M 16/1075 128/205.25 |

* cited by examiner

*Primary Examiner* — Margaret M Luarca
(74) *Attorney, Agent, or Firm* — Maier & Maier, PLLC

(57) ABSTRACT

Provided is an HFNC system, including at least one first sensor disposed on a first housing, a compensating device disposed on a second housing and a the controller communicatively connected with the at least one first sensor and the compensating device respectively; where the at least one first sensor is configured to collect first sensing data, and send the first sensing data to the controller; the controller is configured to receive the first sensing data, generate a first driving signal according to the first sensing data, and send the first driving signal to the compensating device; and the compensating device is configured to receive the first driving signal, where the first driving signal is used to cause vibration of the compensating device according to the first driving signal, vibration of the second housing caused by vibration of the first housing is compensated by the vibration of the compensating device.

10 Claims, 5 Drawing Sheets

HFNC SYSTEM

TECHNICAL FIELD

The present application relates to the field of signal processing technologies, and particularly to a high flow nasal cannula (HFNC) system.

BACKGROUND

An HFNC system supplies oxygen enriched, heated, humidified gas at high flow rate up to 100 liter per minute (lpm) to support patients. For many patients diagnosed with chronic lung conditions such as chronic obstructive pulmonary disease (COPD), the HFNC system is the most effective treatment device to alleviate respiratory symptoms. Pulmonary fibrosis is a potential consequence of coronavirus disease 2019 (COVID-19), leading to long-lasting respiratory problems and activity limitations, and thus HFNC system is beneficial to improve the symptoms of lung fibrosis.

This background information is provided to reveal information believed by the applicant to be of possible relevance to the present application. No admission is necessarily intended, nor should be construed, that any of the preceding information constitutes prior art against the present application.

SUMMARY

Embodiments of the present application provide an HFNC system, which enhances compliance of patient receiving HFNC treatment, and thus maximizes therapeutic effectiveness of a patient.

The foregoing and other objects are achieved by the subject matter of the independent claims. Further implementation forms are apparent from the dependent claims, the description and the figures.

An embodiment of the present application provides an HFNC system, including: a controller, at least one first sensor, a compensating device, a first housing disposed with the at least one first sensor, and a second housing disposed with the compensating device;
  where the controller is communicatively connected with the at least one first sensor and the compensating device respectively;
  the at least one first sensor is configured to collect first sensing data, and send the first sensing data to the controller;
  the controller is configured to generate a first driving signal according to the first sensing data, and send the first driving signal to the compensating device; and
  the compensating device is configured to receive the first driving signal generated by the controller according to the first sensing data, where the first driving signal is used to cause vibration of the compensating device according to the first driving signal, vibration of the second housing caused by vibration of the first housing is compensated by the vibration of the compensating device.

In a possible implementation, the compensating device is configured to collect second sensing data, and send the second sensing data to the controller, where the second sensing data includes a vibrational amplitude and a vibrational phase of the second housing after the vibration of the second housing is compensated by the vibration of the compensating device;

the controller is configured to:
  receive the second sensing data collected by the compensating device;
  determine whether the vibrational amplitude of the second housing is less than a first threshold value according to the second sensing data; and
  upon determining that the vibrational amplitude of the second housing is not less than the first threshold value, adjust the first driving signal according to the vibrational amplitude and the vibrational phase of the second housing to adjust the vibration of the compensating device.

In a possible implementation, the compensating device includes an actuator and at least one second sensor, the actuator and the at least one second sensor are communicatively connected to the controller respectively.

In a possible implementation, the actuator is disposed in a center of a surface of the second housing.

In a possible implementation, the at least one second sensor includes one second sensor disposed close to a center of a surface of the second housing.

In a possible implementation, the at least one second sensor includes a plurality of second sensors;
  where the plurality of second sensors are disposed randomly on a surface of the second housing, or the plurality of second sensors are disposed on a surface of the second housing in array.

In a possible implementation, the controller is configured to:
  perform an average operation on the second sensing data collected by the plurality of second sensors to obtain averaged second sensing data; and
  determine whether the vibrational amplitude of the second housing is less than the first threshold value according to the averaged second sensing data.

In a possible implementation, the first housing and the second housing are different housings.

In a possible implementation, the first housing is inside the second housing.

In a possible implementation, the first housing and the second housing are the same housing.

In a possible implementation, the HFNC system further includes a sound-producing device and a connecting device;
  where the sound-producing device is disposed on the first housing and configured to supply gas to a user;
  the connecting device includes a gas delivering device operatively connected to the sound-producing device and earplugs communicatively connected to the gas delivering device, the gas delivering device is configured to deliver the gas from the sound-producing device to the user, and the earplugs are configured to perform noise reducing processing on sound from the gas delivering device.

The present application provides an HFNC system including a controller, at least one first sensor, a compensating device, a first housing disposed with the at least one first sensor, and a second housing disposed with the compensating device; where the controller is communicatively connected with the at least one first sensor and the compensating device respectively; the at least one first sensor is configured to collect first sensing data, and send the first sensing data to the controller; the controller is configured to receive the first sensing data collected by the at least one first sensor, generate a first driving signal according to the first sensing data, and send the first driving signal to the compensating device; and the compensating device is configured to receive the first driving signal generated by the controller according to the first sensing data, where the first driving signal is used to cause vibration of the compensating device according to the first driving signal, vibration of the second housing caused by vibration of the first housing is compensated by the vibration of the compensating device. By using the HFNC system provided in the present application, compliance of a patient receiving HFNC treatment is enhanced, and thus therapeutic effectiveness of the patient is maximized.

BRIEF DESCRIPTION OF DRAWINGS

The accompanying drawings are used to provide a further understanding of the present application, constitute a part of the specification, and are used to explain the present application together with the following specific embodiments, but should not be construed as limiting the present application.

DESCRIPTION OF EMBODIMENTS

Figure 1:
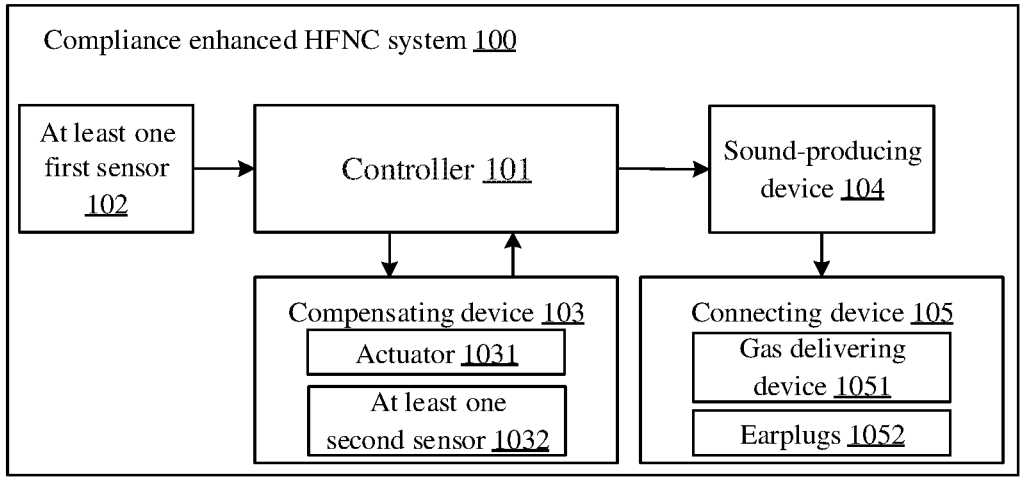
FIG. 1 shows a schematic block diagram of an HFNC system provided by an embodiment of the present application.

In the following description, reference is made to the accompanying figures, which form part of the application, and which show, by way of illustration, specific aspects of embodiments of the present application or specific aspects in which embodiments of the present application may be used. It is understood that embodiments of the present application may be used in other aspects and include structural or logical changes not depicted in the figures. The following detailed description, therefore, is not to be taken in a limiting sense, and the scope of the present application is defined by the appended claims.

In the existing HFNC system, patient compliance is a major issue. Many patients are resistant to HFNC system due to the large noise generated by a blower and/or a compressor of the HFNC system. Such compliance issues are particularly amplified at nighttime because the noise interferes with the sleep of a patient, which is essential to the effective treatment and recovery with respiratory diseases.

The noise issue is intrinsic to the HFNC system, relating to two major factors: 1), the blower and the compressor therein used to generate high flow air, 2) a delivery of high flow air through a nasal cannula piece from the HFNC system to the patient. Among them, the noise from the nasal cannula piece is a broad band noise, while the noise from the blower and the compressor is low frequency narrower band noise.

The present application provides an HFNC system including a controller, at least one first sensor, a compensating device, a first housing disposed with the at least one first sensor, and a second housing disposed with the compensating device; where the controller is communicatively connected with the at least one first sensor and the compensating device respectively; the at least one first sensor is configured to collect first sensing data, and send the first sensing data to the controller; the controller is configured to receive the first sensing data collected by the at least one first sensor, generate a first driving signal according to the first sensing data, and send the first driving signal to the compensating device; and the compensating device is configured to receive the first driving signal generated by the controller according to the first sensing data, where the first driving signal is used to cause vibration of the compensating device according to the first driving signal, vibration of the second housing caused by vibration of the first housing is compensated by the vibration of the compensating device. By using the HFNC system provided in the present application, compliance of a patient receiving HFNC treatment is enhanced, and thus therapeutic effectiveness of the patient is maximized.

It should be noted that, the communication connection herein may be direct connection or indirect connection through some interfaces, apparatuses or units, may be wired connection or wireless connection, and may be electrical, mechanical or otherwise, which is not limited in the present application as long as communication can be realized.

In the following, the technical solutions of the present application will be described in detail with reference to the accompanying drawings.

FIG. 1 shows a schematic block diagram of an HFNC system provided by an embodiment of the present application.

As shown in FIG. 1, the HFNC system 100 includes: a controller 101, at least one first sensor 102, a compensating device 103, a first housing disposed with and the at least one first sensor 102, and a second housing disposed with the compensating device 103; where the controller 101 is communicatively connected with the at least one first sensor 102, the compensating device 103 respectively.

The at least one first sensor 102 is configured to collect first sensing data, and send the first sensing data to the controller 101.

The controller 101 is configured to receive the first sensing data collected by the at least one first sensor 102, generate a first driving signal according to the first sensing data, and send the first driving signal to the compensating device 103.

The compensating device 103 is configured to receive the first driving signal generated by the controller 101 according to the first sensing data, where the first driving signal is used to cause vibration of the compensating device 103 according to the first driving signal, vibration of the second housing caused by vibration of the first housing is compensated by the vibration of the compensating device 103.

In this way, since the at least one first sensor 102 is communicatively connected with the controller and disposed on the first housing, the vibration of the first housing of the first housing can be detected by such sensor and fed back to the controller in form of first sensing data, thereby enabling the controller to generate a first driving signal and send the first driving signal to the compensating device 103 to adjust vibration of the compensating device 103, so that a vibrational amplitude of the compensating device 103 is adjusted to be substantially the same as a vibrational amplitude of the second housing before the vibration of the second housing is compensated by the vibration of the compensating device 103, and a vibrational phase of the compensating device is adjusted to be substantially opposite to a vibrational phase of the second housing before the vibration of the second housing is compensated by the vibration of the compensating device 103. That is, the vibration of the second housing after being compensated by the vibration of the compensating device 103 is minimized. Therefore, by using the HFNC system provided in the present application, compliance of a patient receiving HFNC treatment is enhanced, and thus therapeutic effectiveness of the patient is maximized. That is, the present application provides a compliance enhanced HFNC system.

It should be noted, because the compensating device 103 is disposed on the second housing, the vibration of the first housing will also cause the compensating device 103 to vibrate. However, the vibration of the compensating device 103 above-mentioned refers to vibration of the compensating device 103 according to the first driving signal.

In a possible implementation, the HFNC system includes a sound-producing device 104 disposed on the first housing and configured to supply gas to a user. The sound-producing device 104 may be or may include a blower, a compressor, and the like, that will produce sound when operating that causes vibration of the first housing.

In a possible implementation, the at least one first sensor 102 may be a vibration sensor that senses vibration of the first housing. The vibration sensor may be at least one of an inductive vibration sensor, an eddy current vibration sensor, a capacitive vibration sensor, a resistance strain type vibration sensor, and a piezoelectric vibration acceleration sensor.

In a possible implementation, the first sensing data may be simulation data collected by the at least one first sensor 102, for example, the first sensing data may specifically be a sinusoidal signal, and the first driving signal generated by the controller 101 according to the first sensing data may also be a sinusoidal signal.

In a possible implementation, the compensating device 103 is configured to collect second sensing data, and send the second sensing data to the controller 101, where the second sensing data includes a vibrational amplitude and a vibrational phase of the second housing after the vibration of the second housing is compensated by the vibration of the compensating device;
the controller 101 is configured to:
receive the second sensing data collected by the compensating device 103;
determine whether the vibrational amplitude of the second housing is less than a first threshold value according to the second sensing data; and
upon determining that the vibrational amplitude of the second housing is not less than the first threshold value, adjust the first driving signal according to the vibrational amplitude and the vibrational phase of the second housing to adjust the vibration of the compensating device 103.

In an embodiment, the controller 101 generates the first driving signal by applying an amplitude scaling factor and a phase shifting factor on the first sensing data, and accordingly, the controller 101 adjusts the first driving signal by adjusting the amplitude scaling factor and the phase shifting factor of the first driving signal.

Specifically, the amplitude scaling factor is a factor used to adjust a vibrational amplitude of the first sensing data, and the phase shifting factor is a factor used to adjust a vibrational phase of the first sensing data.

The generation and adjustment of the first driving signal is described by taking the first sensing data being a sinusoidal signal as an example. It is assumed that the first sensing data is represented by $y=A \sin(\omega x+\phi)$, where $A$ is an amplitude of the first sensing data, $\omega$ is a period of the first sensing data, and $\phi$ is a phase of the first sensing data. the controller 101 generates the first driving signal by applying an amplitude scaling factor a and a phase shifting factor b on the first sensing data to obtain the first driving signal represented by $y=aA \sin(\omega x+\phi+b)$. Accordingly, the controller 101 adjusts the first driving signal by adjusting the amplitude scaling factor a and the phase shifting factor b of the first driving signal.

It should be noted that, the above reception, determination and adjustment processes may be performed for only once, or may be performed repeatedly until the vibration of the compensating device 103 is adjusted to a preset level that enables the vibrational amplitude of the second housing to be less than the first threshold value according to the second sensing data, that is, enables the vibration of the second housing after being compensated by the vibration of the compensating device minimum.

Specifically, in a situation where the above reception, determination and adjustment processes is performed for only once, the controller 101 receives the second sensing data collected by the compensating device 103; and determines whether the vibrational amplitude of the second housing is less than the first threshold value according to the second sensing data. When it is determined that the vibrational amplitude of the second housing is less than the first threshold value, the first driving signal is remained unchanged without being adjusted. In this situation, the vibration of the second housing is minimized by performing the above reception, determination and adjustment processes only once.

In another situation, the controller 101 receives the second sensing data collected by the compensating device 103; determines whether the vibrational amplitude of the second housing is less than the first threshold value according to the second sensing data; and when it is determined that the vibrational amplitude of the second housing is not less than the first threshold value, the controller 101 adjusts the first driving signal according to the vibrational amplitude and the vibrational phase of the second housing to adjust the vibration of the compensating device.

The adjustment process is described by taking an example where the controller 101 adjusts the amplitude scaling factor a and the phase shifting factor b in $y=aA \sin(\omega x+\phi+b)$. When it is determined that the vibrational amplitude of the second housing is not less than the first threshold value, the controller 101 determines a reason for the vibrational amplitude of the second housing being not less than the first threshold value according to the vibrational amplitude and the vibrational phase of the second housing, and adjusts at least one of the amplitude scaling factor a and the phase shifting factor b according to the reason.

Then, the controller 101 performs a second round of reception, determination and adjustment processes, which is performed in the same way as the first round, and is not repeated for the sake of conciseness. When it is determined that the vibrational amplitude of the second housing is less than the first threshold value, the circulation ends. However, when it is determined that the vibrational amplitude of the second housing is not less than the first threshold value, the controller 101 further performs a third round, or even one or more further rounds, of reception, determination and adjustment processes again, which is performed in the same way as the first and second rounds, and is not repeated for the sake of conciseness. In this situation, the reception, determination and adjustment processes are performed repeatedly until the vibration of the second housing is minimized.

It should be noted that, the specific adjustment method is not limited in the present application as long as the vibrational amplitude of the second housing is less than the first threshold value after one or more round of reception, determination and adjustment processes.

Figure 2:
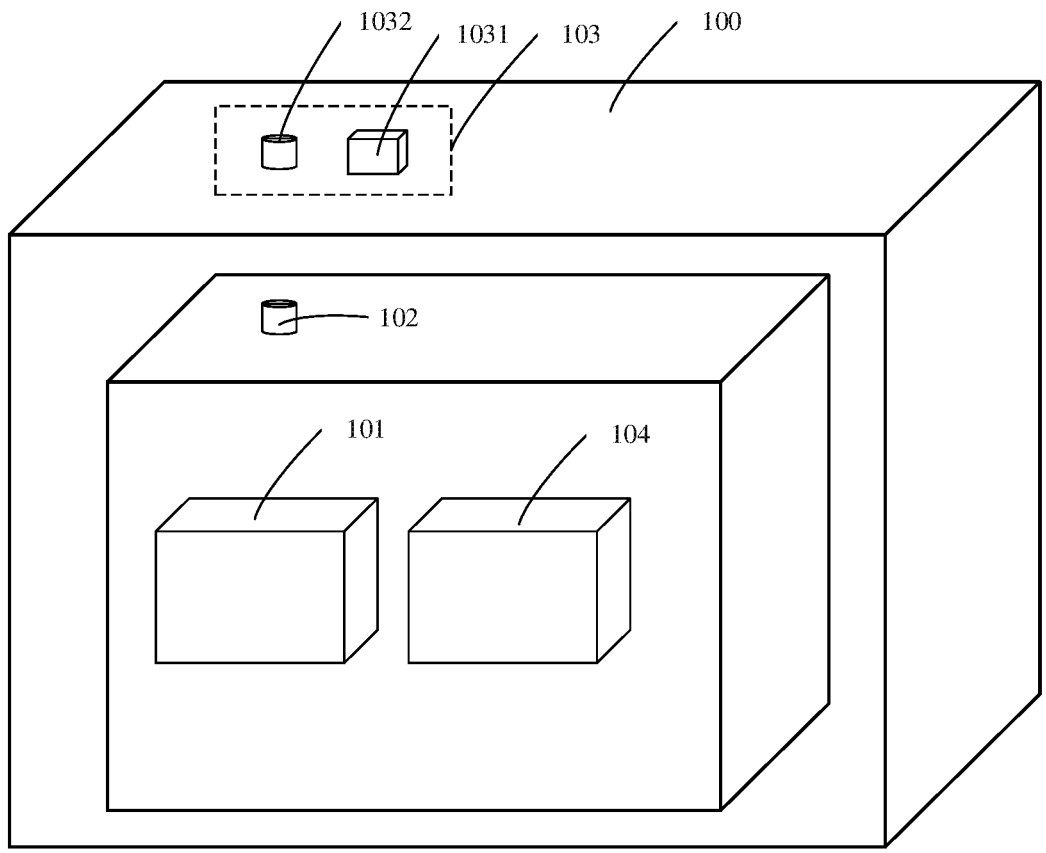
FIG. 2 shows a first schematic structural diagram of an HFNC system provided by an embodiment of the present application.

In a possible implementation, as shown in FIG. 2, which shows a first schematic structural diagram of an HFNC system provided by an embodiment of the present application, the compensating device 103 includes an actuator 1031 and at least one second sensor 1032, the actuator 1031 and the at least one second sensor 1032 are communicatively connected to the controller 101 respectively.

In a possible implementation, the actuator 1031 is disposed in a center of a surface of the second housing.

In this way, the vibration of the compensating device is uniform.

In a possible implementation, the at least one second sensor 1032 includes one second sensor 1032 disposed close to a center of a surface of the second housing.

In this way, the second sensing data collected by the compensating device, specifically the at least one second sensor 1032, is more accurate.

In a possible implementation, the at least one second sensor 1032 includes a plurality of second sensors 1032;
where the plurality of second sensors 1032 are disposed randomly on a surface of the second housing, or the plurality of second sensors 1032 are disposed on a surface of the second housing in array.

In this way, the plurality of second sensors 1032 may respectively collect second sensing data, which may reflect vibration of the second housing in a more realistic way.

In an embodiment, the plurality of second sensors 1032 are disposed randomly on a certain area of a surface of the second housing, or the plurality of second sensors 1032 are disposed on a certain area of a surface of the second housing in array. The certain area could be an area close to a center of a surface of the second housing, or other area of a surface of the second housing, which is not limited in the present application.

In a possible implementation, the at least one second sensor 1032 includes a plurality of second sensors 1032;
where the plurality of second sensors 1032 are disposed on a surface of the second housing in a preset layout.

For example, in case that there are four second sensors 1032, the four second sensors 1032 may be disposed on four corners of a surface of the second housing, respectively. For another example, in case that there are five second sensors 1032, one second sensor 1032 may be disposed in a center of a surface of the second housing, and the remaining four second sensors 1032 may be disposed on four corners of the surface of the second housing, respectively.

In a possible implementation, the controller 101 is configured to:
perform an average operation on the second sensing data collected by the plurality of second sensors 1032 to obtain averaged second sensing data; and
determine whether the vibrational amplitude of the second housing is less than the first threshold value according to the averaged second sensing data.

Specifically, the controller 101 may perform an arithmetic average operation or a weighted average operation on the second sensing data collected by the plurality of second sensors 1032 to obtain the averaged second sensing data. It should be noted that, the controller 101 may perform other average operations on the second sensing data collected by the plurality of second sensors 1032 to obtain the averaged second sensing data, which is not limited in the present application.

In this way, by performing an average operation on the second sensing data collected by the plurality of second sensors, the averaged second sensing data obtained may reflect the vibration of the second housing more accurately.

In a possible implementation, the first housing and the second housing are different housings.

In this way, two housings are provided, so that when the first driving signal is received by the compensating device 103 to adjust vibration of the compensating device 103, because the at least one first sensor 102 and the compensating device 103 are disposed on different housings, the vibration of the first housing would not affect the vibration of the compensating device 103, and compensation of the vibration of the compensating device to the vibration of the second housing caused by vibration of the first housing may be more accurate.

In a possible implementation, the first housing is inside the second housing.

Figure 3:
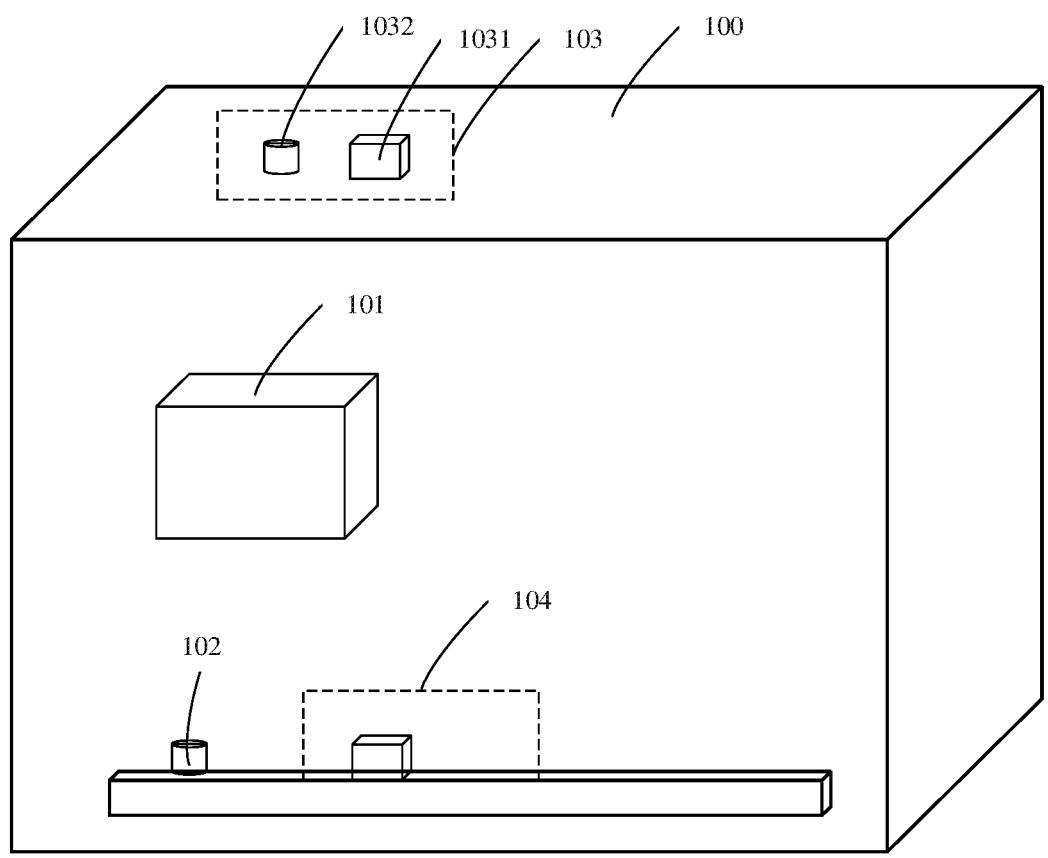
FIG. 3 shows a second schematic structural diagram of an HFNC system provided by an embodiment of the present application.

In an embodiment, as shown in FIG. 3, which shows a second schematic structural diagram of an HFNC system provided by an embodiment of the present application, the first housing is a substrate on which the blower of the sound-producing device 104 and the at least one first sensor 102 are disposed and disposed inside the second housing.

In another embodiment, as shown in FIG. 2, the first housing is an inner housing of the HFNC system, and the second housing is an outer housing of the HFNC system. The sound-producing device 104 and the at least one first sensor 102 are disposed on an inner wall of the first housing, and the compensating device 103 is disposed on an outer wall of the second housing. Alternatively, the sound-producing device 104 and the at least one first sensor 102 are disposed on an outer wall of the first housing, and the compensating device 103 is disposed on an inner wall of the second housing. The positions of the sound-producing device 104, the at least one first sensor 102 and the compensating device 103 are not limited in the present application, as long as the sound-producing device 104 and the at least one first sensor 102 are disposed on the first housing, and the compensating device 103 is disposed on the second housing.

In a possible implementation, the first housing and the second housing are the same housing.

In this way, one housing is provided, so that when the first driving signal is received by the compensating device 103 to adjust vibration of the compensating device 103, because the at least one first sensor 102 and the compensating device 103 are disposed on the same housing, the vibration of the first housing may directly cause the vibration of the second housing without any vibration loss caused due to ambient diffusion, the compensation effect is better.

In a possible implementation, the second housing may be a hexahedron housing. In order to minimize the sound produced by the sound-producing device 104 in a faster and more accurate way, the compensating device 103 is disposed on a first surface of the second housing, and the HFNC system may further include at least one further compensating device respectively disposed on at least one of the other surfaces of the second housing. Accordingly, at least one further sensor, cooperate with the at least one further compensating device respectively, is disposed on the first housing.

It should be noted that the number of components respectively included in the compensating devices of the HFNC system (namely the at least one further compensating device and the compensating device 103) may be all the same, partly the same, or may be different from each other, and the number of the sensors of the HFNC system (namely the at least one further sensor respectively cooperating with the at least one further compensating device and the at least one sensor 102) may be all the same, partly the same, or may be different from each other. This is not limited in the present application as long as the controller 101 can receive sensing data collected by the at least one further sensor and generate driving signal to respectively adjust vibration of the corresponding further compensating device, so as to minimize the vibration of the first housing.

Figure 4:
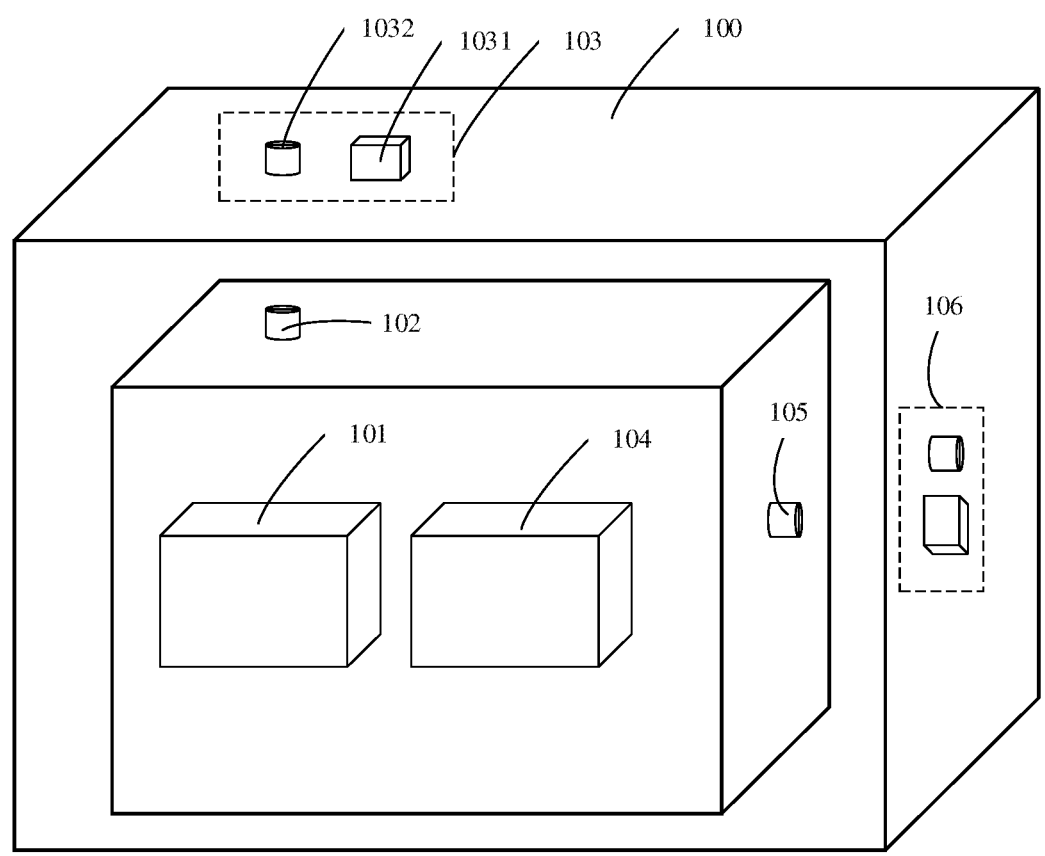
FIG. 4 shows a third schematic structural diagram of an HFNC system provided by an embodiment of the present application.

FIG. 4 is a third schematic structural diagram of an HFNC system provided by an embodiment of the present application. As shown in the embodiment shown in FIG. 4, the first housing and the second housing are hexahedron housings, the HFNC system further includes at least one third sensor 105, a further compensating device 106, the at least one first sensor 102 is disposed on a first surface of the first housing, the at least one third sensor 105 is disposed on a second surface of the first housing, the compensating device 103 is disposed on a first surface of the second housing, the further compensating device 106 is disposed on a second surface of the second housing; where the controller 101 is communicatively connected with the at least one third sensor 105 and the further compensating device 106 respectively.

The at least one third sensor 105 is configured to collect third sensing data, and send the third sensing data to the controller 101.

The controller 101 is configured to receive the third sensing data collected by at least one third sensor 105, generate a second driving signal according to the third sensing data, and send the second driving signal to the further compensating device 106.

The further compensating device 106 is configured to receive the second driving signal generated by the controller 101 according to the third sensing data, where the first driving signal is used to cause adjustment of vibration of the further compensating device 106 according to the second driving signal, vibration of the second housing caused by vibration of the second surface of the first housing is compensated by the vibration of the further compensating device 106.

In this way, the vibration of the second surface of the second housing caused by the vibration of the first surface of the first housing is compensated by the vibration of the compensating device 103, and the vibration of the second surface of the second housing caused by the vibration of the second surface of the first housing is compensated by the vibration of the further compensating device 106, which may minimize the sound produced by the sound-producing device 104 in a faster way.

It should be noted that, the structure and operation of the further compensating device 106 are the same as the first compensating device 103, which is not repeated herein.

It should also be noted that, at least two surfaces of the first housing and at least two surfaces of the second housing are disposed with sensors, and the number of the surfaces of the first housing disposed with sensors is the same as the number of the surfaces of the second housing disposed with sensors.

Specifically, in the embodiment shown in FIG. 4, the at least one first sensor 102 and the at least one third sensor 105 are respectively disposed on the first surface and the second surfaces of the first housing, and the compensating device 103 and the further compensating device 106 are respectively disposed on the first surface and the second surfaces of the second housing.

In another embodiment, based on the embodiment shown in FIG. 4, three surfaces of the first housing and three surfaces of the second housing are disposed with sensors, or four surfaces of the first housing and four surfaces of the second housing are disposed with sensors, and so on, as long as the number of the surfaces of the first housing disposed with sensors is the same as the number of the surfaces of the second housing disposed with sensors.

In an embodiment, the compensating device 103 includes a plurality of second sensors 1032, the further compensating device 106 includes a plurality of fourth sensors (not shown), the plurality of second sensors 1032 may be disposed randomly on the first surface of the second housing, or disposed on the first surface of the second housing in array, or disposed on the first surface of the second housing in a preset layout, the plurality of fourth sensors may be disposed randomly on the second surface of the second housing, or disposed on the second surface of the second housing in array, or disposed on the second surface of the second housing in a preset layout.

It should be noted that, the layout of the plurality of second sensors 1032 on the first surface of the second housing and the layout of the plurality of fourth sensors on the second surface of the second housing may be the same, or different, which is not limited in the present application.

Figure 5:
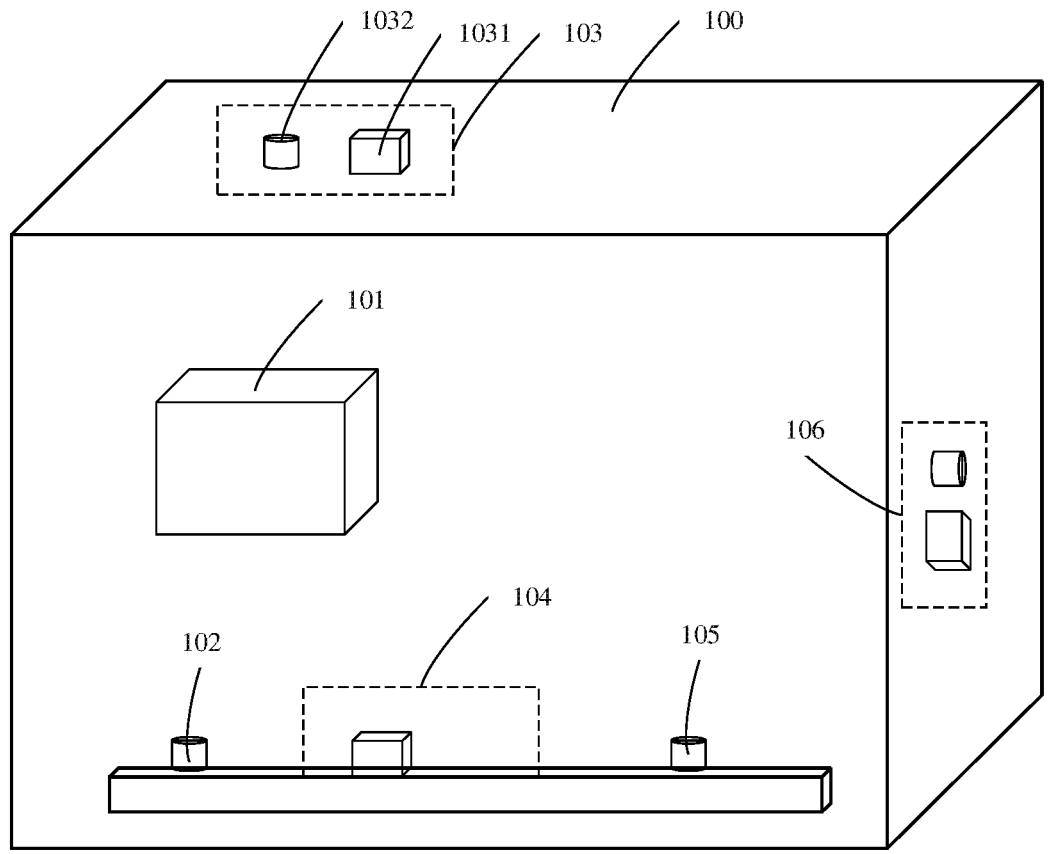
FIG. 5 shows a fourth schematic structural diagram of an HFNC system provided by an embodiment of the present application.

FIG. 5 shows a fourth schematic structural diagram of an HFNC system provided by an embodiment of the present application. The embodiment shown in FIG. 5 is the same as the embodiment shown in FIG. 4 except that the first housing is a substrate on which the blower of the sound-producing device 104 and the at least one first sensor 102 and the at least one third sensor 105 are disposed.

In another embodiment, based on the embodiment shown in FIG. 5, more than two surfaces of the second housing are disposed with sensors.

In a possible implementation, the HFNC system further includes a sound-producing device 104 and a connecting device 105;

where the sound-producing device 104 is disposed on the first housing and configured to supply gas to a user;
the connecting device 105 includes a gas delivering device 1051 operatively connected to the sound-producing device 104 and earplugs 1052 communicatively connected to the gas delivering device 1051, the gas delivering device 1051 is configured to deliver the gas from the sound-producing device 104 to the user, and the earplugs 1052 are configured to perform noise reducing processing on sound from the gas delivering device 1051.

The sound-producing device 104 may provide oxygen, compressed air, nitrogen, nitrous oxide, carbon dioxide and other gases according to actual needs.

In an embodiment, the gas delivering device 1051 includes a nasal cannula piece inserted into a nose of the user and a head fixator, where the nasal cannula piece is connected with a head of the user through the head fixator, and the earplugs 1052 covers the head fixator upon being ware by the user. The head fixator may, for example, be a bandage.

In another embodiment, the gas delivering device 1051 further includes a gas pathway, where one end of the gas pathway is connected with the sound-producing device 104, and the other end of the gas pathway is connected with the nasal cannula piece.

In a possible implementation, the earplugs 1052 includes at least one microphone, at least one speaker and a microcontroller;

where the at least one microphone is configured to collect noise data generated by the gas delivering device 1051, and send the noise data to the microcontroller; and the microcontroller is configured to generate an inverse signal, and send the inverse signal to the at least one speaker to produce sound which compensates noise from the gas delivering device 1051.

In this way, the noise heard by the patient from the gas delivering device 1051 can be reduce, which further enhances the compliance of the patient receiving HFNC treatment, and maximizes the therapeutic effectiveness of the patient.

Figure 6:
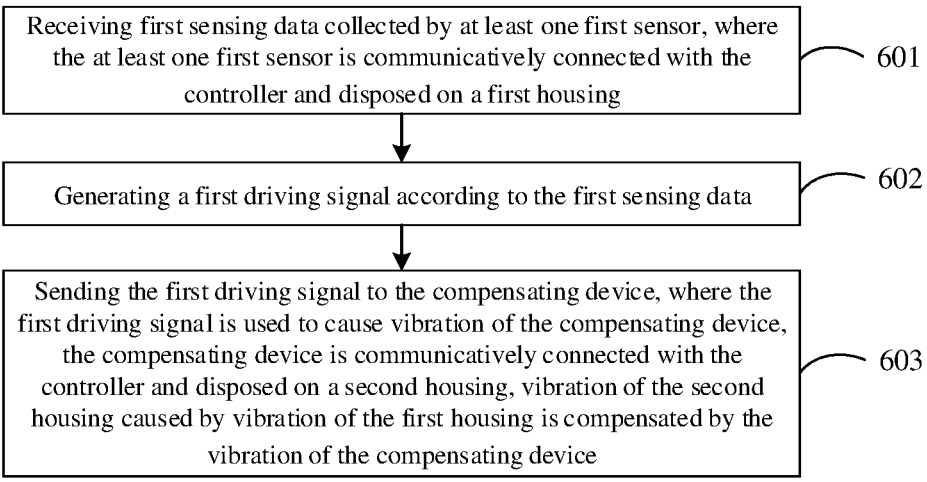
FIG. 6 illustrates a schematic flowchart of a method for reducing noise according to an embodiment of the present application.

An embodiment of the present application provides a method for reducing noise, the method is executed by a controller. FIG. 6 illustrates a schematic flowchart of a method for reducing noise according to an embodiment of the present application. As shown in FIG. 6, the method includes the following steps.

Step 601: receiving first sensing data collected by at least one first sensor, where the at least one first sensor is communicatively connected with the controller and disposed on a first housing.

Step 602: generating a first driving signal according to the first sensing data.

Step 603: sending the first driving signal to the compensating device, where the first driving signal is used to cause vibration of the compensating device, the compensating device is communicatively connected with the controller and disposed on a second housing, vibration of the second housing caused by vibration of the first housing is compensated by the vibration of the compensating device.

In a possible implementation, the method further includes:

receiving a second sensing data collected by the compensating device, where the second sensing data includes a vibrational amplitude and a vibrational phase of the second housing after the vibration of the second housing is compensated by the vibration of the compensating device;

determining whether the vibrational amplitude of the second housing is less than a first threshold value according to the second sensing data; and upon determining that the vibrational amplitude of the second housing is not less than the first threshold value, adjust the first driving signal according to the vibrational amplitude and the vibrational phase of the second housing to adjust the vibration of the compensating device.

In a possible implementation, the compensating device includes an actuator and at least one second sensor, the actuator and the at least one second sensor are communicatively connected to the controller respectively, the at least one second sensor includes a plurality of second sensors, the determining whether the vibrational amplitude of the second housing is less than the first threshold value according to the second sensing data includes:

performing an average operation on the second sensing data collected by the plurality of second sensors to obtain averaged second sensing data; and determining whether the vibrational amplitude of the second housing is less than the first threshold value according to the averaged second sensing data.

In a possible implementation, the controller is applied in an HFNC system including a sound-producing device, and the sound-producing device is disposed on the first housing.

Figure 7:
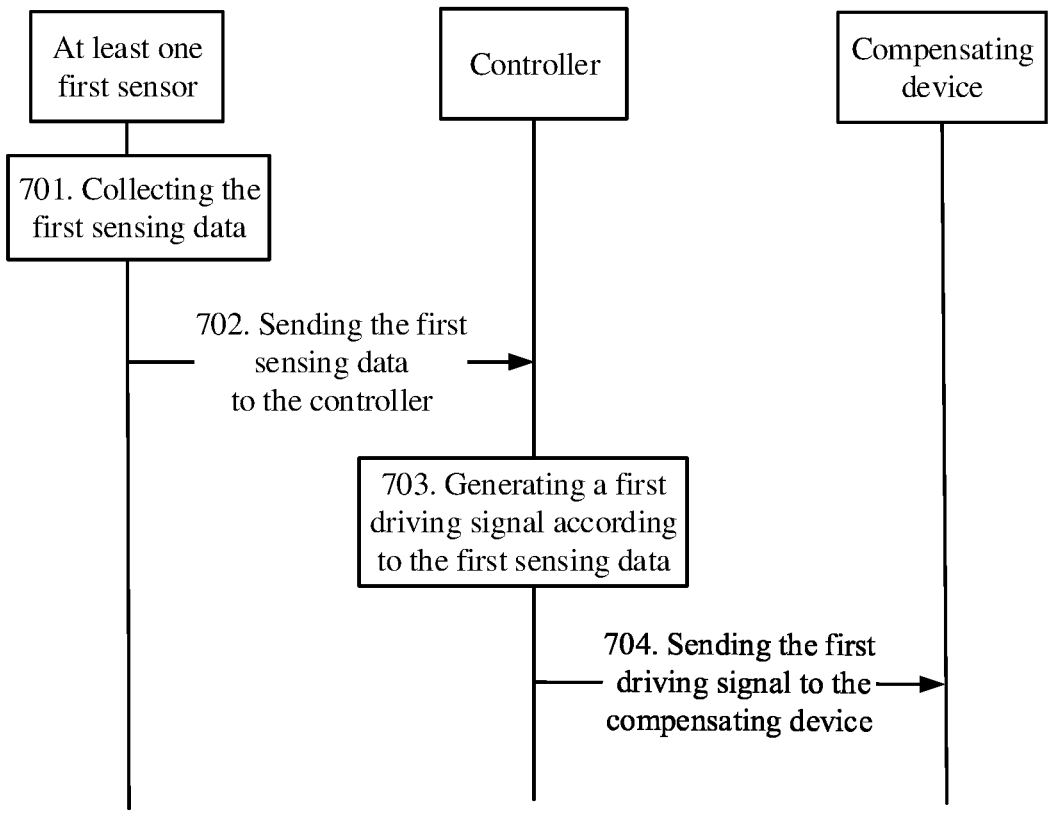
FIG. 7 illustrates a schematic flowchart of a method for reducing noise according to another embodiment of the present application.

An embodiment of the present application provides a method for reducing noise, the method is executed by an HFNC system, where the HFNC system includes a controller, at least one first sensor, a sound-producing device, a compensating device, a first housing disposed with the sound-producing device and the at least one first sensor, and a second housing disposed with the compensating device. FIG. 7 illustrates a schematic flowchart of a method for reducing noise according to another embodiment of the present application. As shown in FIG. 7, the method includes the following steps.

Step 701: the at least one first sensor collects the first sensing data.

Step 702: the at least one first sensor send the first sensing data to the controller.

Step 703: the controller generates a first driving signal according to the first sensing data.

Step 704: the controller sends the first driving signal to the compensating device, where the first driving signal is used to cause vibration of the compensating device according to the first driving signal, vibration of the second housing caused by vibration of the first housing is compensated by the vibration of the compensating device.

In a possible implementation, the method further includes:

the compensating device collecting a second sensing data, where the second sensing data includes a vibrational amplitude and a vibrational phase of the second housing after the vibration of the second housing is compensated by the vibration of the compensating device;

the compensating device sending the second sensing data to the controller;

the controller determining whether the vibrational amplitude of the second housing is less than a first threshold value according to the second sensing data; and upon determining that the vibrational amplitude of the second housing is not less than the first threshold value, the controller adjusting the first driving signal according to the vibrational amplitude and the vibrational phase of the second housing to adjust the vibration of the compensating device.

In a possible implementation, the compensating device includes an actuator and at least one second sensor, the actuator and the at least one second sensor are communicatively connected to the controller respectively, the at least one second sensor includes a plurality of second sensors, the controller determines the vibrational amplitude of the second housing is less than the first threshold value according to the second sensing data by:

performing an average operation on the second sensing data collected by the plurality of second sensors to obtain averaged second sensing data; and determine whether the vibrational amplitude of the second housing is less than the first threshold value according to the averaged second sensing data.

Figure 8:
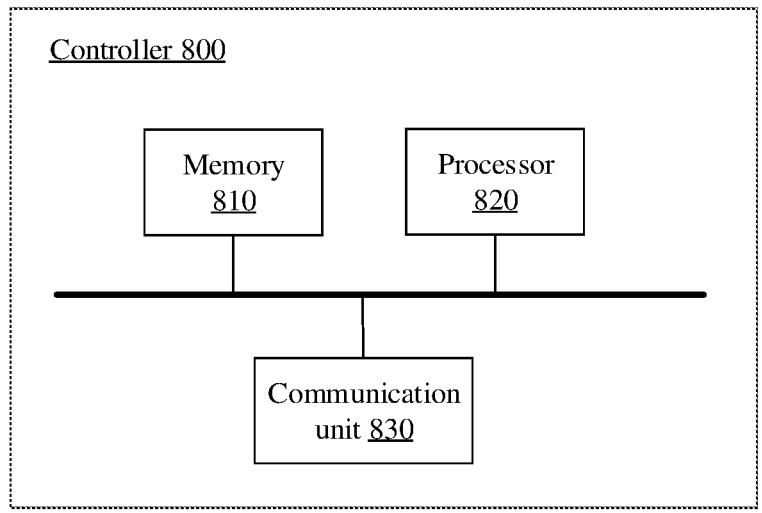
FIG. 8 illustrates a schematic structural diagram of a controller provided by an embodiment of the present application.

FIG. 8 illustrates a schematic structural diagram of a controller provided by an embodiment of the present application. As shown in FIG. 8, a controller 800 may include a memory 810 and a processor 820, where a computer program is stored in the memory 810, and configured to be executed by the processor 820 to implement the steps described in the above embodiments. In addition, the controller 800 may further include a communication unit 830 for communicating with the at least one first sensor 102 and the compensating device 103. The computer program (also known as programs, software, software applications, or codes) include machine instructions for a programmable processor, and may be implemented using high-level procedural and subtended programming languages, or assembly/machine languages.

It should be understood by a person skilled in the art that, the relevant description of the above steps in the embodiments of the present application may be understood with reference to the relevant description of the method for monitoring a condition of a patient in the embodiments of the present application.

The term such as "and/or" in the embodiments of the present application is merely used to describe an association between associated objects, which indicates that there may be three relationships, for example, A and/or B may indicate presence of A only, of both A and B, and of B only.

The term "a" or "an" is not intended to specify one or a single element, instead, it may be used to represent a plurality of elements where appropriate.

In the embodiments of the present application, expressions such as "exemplary" or "for example" are used to indicate illustration of an example or an instance. In the embodiments of the present application, any embodiment or design scheme described as "exemplary" or "for example" should not be interpreted as preferred or advantageous over other embodiments or design schemes. In particular, the use of "exemplary" or "for example" is aimed at presenting related concepts in a specific manner.

It should be appreciated that, steps may be reordered, added, or deleted according to the various processes described above. For example, the steps described in the present application may be executed in parallel, sequentially, or in different orders, which are not limited herein as long as the desired results of the technical solutions disclosed in the present application can be achieved.

Finally, it should be noted that the foregoing embodiments are merely intended for describing the technical solutions of the present application other than limiting the present application. Although the present application is described in detail with reference to the foregoing embodiments, a person of ordinary skill in the art should understand that he may still make modifications to the technical solutions described in the foregoing embodiments, or make equivalent replacements to some technical features thereof, without departing from the spirit and scope of the technical solutions of the embodiments of the present application.

What is claimed is:

1. A high flow nasal cannula (HFNC) system, comprising: a controller, at least one first sensor, a compensating device, a first housing disposed with the at least one first sensor, and a second housing disposed with the compensating device;
wherein the controller is communicatively connected with the at least one first sensor and the compensating device respectively;
the at least one first sensor is configured to collect first sensing data, and send the first sensing data to the controller;
the controller is configured to receive the first sensing data collected by the at least one first sensor, generate a first driving signal according to the first sensing data, and send the first driving signal to the compensating device;
the compensating device is configured to receive the first driving signal generated by the controller according to the first sensing data, wherein the first driving signal is used to cause vibration of the compensating device according to the first driving signal, vibration of the second housing caused by vibration of the first housing is compensated by the vibration of the compensating device; and wherein the compensating device comprises an actuator and at least one second sensor, the actuator and the at least one second sensor are communicatively connected to the controller respectively.

2. The HFNC system according to claim 1, wherein the compensating device is configured to collect second sensing data, and send the second sensing data to the controller, wherein the second sensing data comprises a vibrational amplitude and a vibrational phase of the second housing after the vibration of the second housing is compensated by the vibration of the compensating device;
the controller is configured to:
receive the second sensing data collected by the compensating device;
determine whether the vibrational amplitude of the second housing is less than a first threshold value according to the second sensing data; and
upon determining that the vibrational amplitude of the second housing is not less than the first threshold value, adjust the first driving signal according to the vibrational amplitude and the vibrational phase of the second housing to adjust the vibration of the compensating device.

3. The HFNC system according to claim 2, wherein the actuator is disposed in a center of a surface of the second housing.

4. The HFNC system according to claim 2, wherein the at least one second sensor comprises one second sensor disposed close to a center of a surface of the second housing.

5. The HFNC system according to claim 2, wherein the at least one second sensor comprises a plurality of second sensors;
wherein the plurality of second sensors are disposed randomly on a surface of the second housing, or the plurality of second sensors are disposed on a surface of the second housing in array.

6. The HFNC system according to claim 5, wherein the controller is configured to:
perform an average operation on the second sensing data collected by the plurality of second sensors to obtain averaged second sensing data; and
determine whether the vibrational amplitude of the second housing is less than the first threshold value according to the averaged second sensing data.

7. The HFNC system according to claim 1, wherein the first housing and the second housing are different housings.

8. The HFNC system according to claim 7, wherein the first housing is inside the second housing.

9. The HFNC system according to claim 1, wherein the first housing and the second housing are the same housing.

10. The HFNC system according to claim 1, wherein the HFNC system further comprises a sound-producing device and a connecting device;
wherein the sound-producing device is disposed on the first housing and configured to supply gas to a user;
the connecting device comprises a gas delivering device operatively connected to the sound-producing device and earplugs communicatively connected to the gas delivering device, the gas delivering device is configured to deliver the gas from the sound-producing device to the user, and the earplugs are configured to perform noise reducing processing on sound from the gas delivering device.

* * * * *